(12) United States Patent
Merkel et al.

(10) Patent No.: US 10,889,539 B2
(45) Date of Patent: Jan. 12, 2021

(54) ANILINE PURIFICATION PROCESS

(71) Applicant: COVESTRO DEUTSCHLAND AG, Leverkusen (DE)

(72) Inventors: Michael Merkel, Düsseldorf (DE); Friedhelm Steffens, Leverkusen (DE); Murat Kalem, Neuss (DE); Peter Lehner, Mülheim an der Ruhr (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 16/654,303

(22) Filed: Oct. 16, 2019

(65) Prior Publication Data
US 2020/0123097 A1   Apr. 23, 2020

(30) Foreign Application Priority Data
Oct. 17, 2018   (EP) .................................... 18200968

(51) Int. Cl.
*C07C 209/84* (2006.01)
*B01D 3/14* (2006.01)
(Continued)

(52) U.S. Cl.
CPC .............. *C07C 209/84* (2013.01); *B01D 3/14* (2013.01); *B01D 3/36* (2013.01); *B01D 5/006* (2013.01); *C07C 211/46* (2013.01)

(58) Field of Classification Search
None
See application file for complete search history.

(56) References Cited

U.S. PATENT DOCUMENTS

| 3,136,818 A | 6/1964 | Sperber et al. |
| 3,682,782 A | 8/1972 | Choo |

(Continued)

FOREIGN PATENT DOCUMENTS

| JP | 08295654 H | 11/1996 |
| JP | 2007217405 A | 8/2007 |

OTHER PUBLICATIONS

European Search Report, EP 18200968, dated Apr. 17, 2019.
(Continued)

*Primary Examiner* — Clinton A Brooks
(74) *Attorney, Agent, or Firm* — Donald R. Palladino (57) ABSTRACT

The present invention concerns a process for the preparation of pure aniline, comprising the steps of a) providing a crude aniline fraction containing up to 20.000% by weight of phenol; b) dividing the crude aniline fraction from step a) into a first partial stream and a second partial stream; c) distilling the first partial stream from step b) in a first distillation column and distilling the second partial stream from step b) in a second distillation column, wherein the first distillation column is operated at a higher head pressure than the second distillation column, with the proviso that each of the first distillation column and the second distillation column is operated at a head pressure in the range from 1.0 $mbar_{(abs.)}$ to 500 $mbar_{(abs.)}$, and wherein from each of the first distillation column and the second distillation column, (i) a gaseous aniline distillate (=purified aniline) is removed as the overhead product and subsequently condensed, wherein a first partial stream of the condensed aniline distillate is returned to the first and/or the second distillation column as a reflux stream and a second partial stream of the condensed aniline distillate is removed as the product stream, and (ii) a liquid bottom stream which is concentrated in phenol is removed, from which a first portion is partially or completely vaporised and is returned to the respective distillation column, and from which a second portion is
(Continued)

discharged; d) using the heat released during the condensation of the aniline distillate from the first distillation column in order to provide the heat necessary for vaporising the first portion of the bottom stream from the second distillation column.

15 Claims, 2 Drawing Sheets

(51) Int. Cl.
    *B01D 3/36*    (2006.01)
    *B01D 5/00*    (2006.01)
    *C07C 211/46*    (2006.01)

(56) References Cited

U.S. PATENT DOCUMENTS

| | | |
|---|---|---|
| 3,871,445 A | 3/1975 | Wanka et al. |
| 5,808,157 A | 9/1998 | Langer et al. |
| 5,877,350 A | 3/1999 | Langer et al. |
| 7,049,471 B2 | 5/2006 | Renner et al. |
| 7,575,660 B2 | 8/2009 | Steffens et al. |
| 8,455,691 B2 | 6/2013 | Sommer et al. |
| 2005/0080294 A1 | 4/2005 | Dubnansky et al. |
| 2005/0263385 A1 | 12/2005 | Steffens et al. |
| 2009/0065347 A1 | 3/2009 | Sommer et al. |
| 2010/0324336 A1 | 12/2010 | Sommer et al. |
| 2015/0080610 A1 | 3/2015 | Merkel et al. |

OTHER PUBLICATIONS

Jander, G. et al., Maßanalyse : Theorie und Praxis der Titrationen mit chemischen und physikalischen Indikationen, 2009, Issue 17, de Gruyter, Berlin, p. 279-282.

ANILINE PURIFICATION PROCESS

CROSS-REFERENCE TO RELATED APPLICATION

This application claims priority to European Application No. 18200968.8, filed Oct. 17, 2018, which is incorporated herein by reference.

FIELD

The present invention relates to a process for the preparation of pure aniline, comprising the steps of a) providing a crude aniline fraction containing, with respect to the total weight of aniline and phenol in the crude aniline fraction, 80.000% by weight to 99.999% by weight of aniline and 0.001% by weight to 20.000% by weight of phenol; b) dividing the crude aniline fraction from step a) into a first partial stream and a second partial stream; c) distilling the first partial stream from step b) in a first distillation column and distilling the second partial stream from step b) in a second distillation column, wherein the first distillation column is operated at a higher head pressure than the second distillation column, with the proviso that each of the first distillation column and the second distillation column is operated at a head pressure in the range from 1.0 $mbar_{(abs.)}$ to 500 $mbar_{(abs.)}$, preferably in the range from 10 $mbar_{(abs.)}$ to 400 $mbar_{(abs.)}$, and wherein from each of the first distillation column and the second distillation column, (i) a gaseous aniline distillate (=purified aniline) is removed as the overhead product and subsequently condensed, wherein a first partial stream of the condensed aniline distillate is returned to the first and/or the second distillation column as a reflux stream and a second partial stream of the condensed aniline distillate is removed as the product stream, and (ii) a liquid bottom stream which is concentrated in phenol is removed, from which a first portion is partially or completely vaporised and is returned to the respective distillation column, and from which a second portion is discharged; d) using the heat released during the condensation of the gaseous aniline distillate from the first distillation column to provide the heat necessary for vaporising the first portion of the bottom stream from the second distillation column.

BACKGROUND

Aniline is an important intermediate product, for example in the manufacture of diisocyanates and polyisocyanates in the diphenylmethane (MDI) series, and is manufactured on an industrial scale usually by the catalytic hydrogenation of nitrobenzene in the gas or liquid phase (see, for example, DE-A 2201528, U.S. Pat. No. 3,136,818, EP-A-0696573 and EP-A-0696574). In this reaction, in addition to the target product aniline, secondary components such as, for example, phenol or aminophenols are also formed which have to be removed prior to further use of the aniline in subsequent processes. The separation of such secondary components, which have boiling points which are very similar to those of the amine to be produced, is particularly problematic, because in this case the distillation expenditure is substantial. In the case of the production of aniline (boiling point at normal pressure 184° C.), the separation of phenol (boiling point at normal pressure 182° C.) in particular is a major challenge for distillation technology, as reflected by the use of long distillation columns with a large number of separation stages and high reflux ratios and a correspondingly high expenditure of energy. A vacuum distillation to remove phenol from aniline is described in DE1935363, for example.

For this reason, there is no shortage of strategies for separating phenol (and other phenolic compounds) from aniline in other ways, in particular by conversion into phenolate salts by reaction with suitable bases. The phenolate salts formed in this manner can be separated from aniline substantially more easily than the phenolic compounds per se, because the former are non-volatile, readily water-soluble compounds.

Thus, JP-A-49-035341 describes a process in which aniline is brought into contact with solid alkali hydroxides in a solid bed and only then conveyed into the distillation, or in which the distillation is carried out in the presence of the solid alkali hydroxide in proportions of 0.1% to 3% by weight with respect to the quantity of aniline to be distilled. In this manner, the separation of critical components such as the aminophenols is facilitated. However, the disadvantage with that process is the use of high molar excesses of the solid alkali hydroxide compared with the acidic secondary components which are to be removed and the impossibility of obtaining an exact dosage of the alkaline compounds. On the one hand, in the case of overdosing, this can result in corrosion problems, precipitation and highly viscous bottom phases in the distillation column and on the other hand, in the case of underdosing, this can result in incomplete removal of the critical components.

US-A-2005 080294 describes a process for separating compounds containing phenolic hydroxy groups from aromatic amines, wherein prior to distillation, a base is added to the amine to be purified in a molar ratio of 1:1 up to 4:1 with respect to the phenolic compounds, optionally in the presence of polyols such as polyethylene glycol, for example. For aniline itself, which is produced in very large quantities, however, an addition of polyols of that type is disadvantageous from an economic viewpoint and there is a risk that the product could be contaminated with polyols/polyol fragments. However, not adding a polyol of that type means that the process could be frequently interrupted due to the precipitation of salts.

EP-A-1 845 079 describes a process for the purification of aniline by adding an aqueous alkali metal hydroxide solution before or during distillation, whereupon problems due to the precipitation of solids, fouling and/or steep rises in viscosity upon distillation are avoided by partially discharging the bottom phase from the distillation, washing it with water or dilute alkali hydroxide solution and returning the washed organic phase to the distillation. The disadvantage therein is the necessity for an additional step of the process in order to maintain reliable operation. Furthermore, in that process, there is an additional effluent stream which is loaded with organics, which has to be worked up and disposed of.

EP-A-2 028 176 describes a process for purifying aromatic amines, in which the crude amine obtained after separation of the process water is supplemented with aqueous alkali metal hydroxide solution and the product of the process obtained in this manner is distilled. The bottoms from the distillation column are partially to completely discharged and partially vaporised via two evaporators (E1) and (E2) connected in series or in parallel. In this manner, a maximum depletion of the valuable amine may be obtained in the bottoms from the distillation column with a minimum of expenditure regarding equipment and energy.

In all of the processes mentioned so far, the aromatic amine is distilled in the presence of a base. In this type of process, problems due to corrosion, solids precipitation and/or fouling during distillation have to be avoided using complicated and/or expensive measures.

In addition, processes exist in which the phenol is removed by extraction with aqueous bases. Nevertheless, in order to remove other non-acidic impurities, the aniline has to be at least partially distilled. Processes of that type have been described, for example, in DE102009025374, JP-A-08-295654 or also in EP 2 641 892 A1. In order to comply with current regulations regarding purity, several extraction stages are necessary as a rule, as described, for example, in JP-A-2007217405; this further complicates matters. Furthermore, in all of those processes, the streams of effluent containing phenolates are substantial, and again, these have to be carefully worked up and disposed of.

Finally, DE 10 2004 026626 describes a process in which an aqueous amine solution is purified in two distillation columns connected in series. In it, one of the columns is operated at 2 to 20 bar and the other is operated at 0.1 to 10 bar. The condensation heat from the vapours which leave the column which is operated at the higher pressure are in this case used to heat the bottom of the column which is operated at a lower pressure. The amine is the bottom product. Therefore, the process is not suitable for the separation of high boilers or phenol from aniline. Moreover, because of the high pressure, high bottom temperatures are necessary, which could result in a partial decomposition of the product and thus to loss of yields or to fouling.

There is therefore a need for further improvements in the field of aniline purification. In particular, accomplishing the separation of compounds which have high boiling points compared with aniline, in particular phenol, in an efficient, energy-saving manner is desirable. Avoiding a treatment of the aniline with a base as far as possible is also desirable.

SUMMARY

In the light of the foregoing, in one aspect, the present invention provides a process for the preparation of pure aniline, comprising the following steps:
a) providing a crude aniline fraction containing, with respect to the total weight of aniline and phenol in the crude aniline fraction, 80.000% by weight to 99.999% by weight of aniline and 0.001% by weight to 20.000% by weight of phenol, in particular containing, with respect to the total weight of aniline and phenol in the crude aniline fraction, 95.000% by weight to 99.995% by weight of aniline and 0.005% by weight to 5.000% by weight of phenol, preferably 98.000% by weight to 99.990% by weight of aniline and 0.010% by weight to 2.000% by weight of phenol, particularly preferably 99.000% by weight to 99.990% by weight of aniline and 0.010% by weight to 1.000% by weight of phenol, more particularly preferably 99.900% by weight to 99.990% by weight of aniline and 0.010% by weight to 0.100% by weight of phenol, wherein compounds which differ from phenol (which may be present as further impurities, in particular benzene, cyclohexylamine, cyclohexanone, cyclohexanol, aminophenols, diphenylamine, N-cyclohexylaniline and phenylenediamine) are preferably present in a proportion with respect to the total weight of the crude aniline stream of 2.00% by weight, particularly preferably a maximum of 1.00% by weight, particularly preferably a maximum of 0.50% by weight;
b) dividing the crude aniline fraction from step a) into partial streams, and in fact into at least a first partial stream and a second partial stream;
c) distilling the first partial stream from step b) in a first distillation column and distilling the second partial stream from step b) in a second distillation column, wherein the first distillation column is operated at a higher head pressure than the second distillation column, with the proviso that each of the first distillation column and the second distillation column is operated at a head pressure in the range from 1.0 $mbar_{(abs.)}$ to 500 $mbar_{(abs.)}$, preferably in the range from 10 $mbar_{(abs.)}$ to 400 $mbar_{(abs.)}$, particularly preferably in the range from 50 $mbar_{(abs.)}$ to 350 $mbar_{(abs.)}$, and wherein from each of the first distillation column and the second distillation column,
a gaseous aniline distillate is removed as the overhead product and subsequently condensed, wherein a first partial stream of the condensed aniline distillate is returned to the first distillation column and/or the second distillation column as a reflux stream, and a second partial stream of the condensed aniline distillate is removed as the product stream, and
a liquid bottom stream which is concentrated in phenol is removed, from the respective distillation column (in the case of partial vaporisation, the vapour obtained and remaining liquid may be returned separately or together), and from which a second portion is discharged;
d) using the heat released from the condensation of the aniline distillate from the first distillation column to provide the heat necessary for vaporising the first portion of the bottom stream from the second distillation column.

In the context of the present invention, unless stated otherwise, the term contents data for organic compounds refers to values determined by gas chromatography. The quantitative evaluation of gas chromatograms is known to the person skilled in the art. Any potentially necessary methods for the determination of the water content are also known to the person skilled in the art. The prior art methods may also be used in the context of the present invention. In the event of doubt, the water content determined by Karl Fischer titration is decisive. Reference should be made to Jander, Jahr, *Maβanalyse* [*Quantitative Analysis*], issue 17, de Gruyter, Berlin (2009), p. 279 to p. 282 for Karl Fischer titration in general. When determining the water content of aniline fractions (in particular the crude aniline fraction to be provided in step a)), the value determined by Karl Fischer titration after buffering with salicylic acid is decisive. The process using buffering with salicylic acid is also known to the person skilled in the art: see, for example, Merck KGaA, *Wasser in Anilin—Karl Fischer Applikation* [*Water in Aniline—Karl Fischer Application*], 2011, and Honeywell, *HYDRANAL™ Praktikum—Reagenzien nach Eugen Scholz für die Karl-Fischer-Titration* [*HYDRANAL™ Manual: Eugen Scholz reagents for Karl Fischer titration*], 2017).

Here and below, all pressures should be understood to refer to absolute pressures (identified as "$bar_{(abs.)}$").

Expressions such as "a first partial stream and a second partial stream" or "a first distillation column and a second distillation column" or "a first portion and a second portion", unless specifically stated otherwise, should always be interpreted as open formulations which do not exclude the presence of further (third, fourth, etc) partial streams, distillations columns or portions.

The expression "reflux stream" or short "reflux" refers to the part of the condensed head product of a distillation column that is removed as a product stream but is recycled into the distillation column (or, as the case may be, into another distillation column). The expression "reflux ratio" as used in this specification refers to the mass ratio of the reflux stream to the stream that is removed as product stream. The reflux ratio is also referred to as R/E ratio.

Surprisingly, it has been discovered that the problems of the prior art can be solved or at least alleviated when crude aniline, preferably dry crude aniline (i.e. crude aniline with a proportion of water with respect to the total weight of the crude aniline in the range from 0.00% by weight to 0.50% by weight, preferably 0.00% by weight to 0.20% by weight, particularly preferably 0.00% by weight to 0.10% by weight, more preferably 0.00% by weight to 0.05% by weight, especially 0.01% by weight to 0.05% by weight), is distilled in at least two distillation columns operated in parallel with different head pressures, wherein a head pressure of 500 $mbar_{(abs.)}$, preferably 400 $mbar_{(abs.)}$, particularly preferably 350 $mbar_{(abs.)}$, is not exceeded in any of the distillation columns employed (and does not fall below a head pressure of 1.0 $mbar_{(abs.)}$, preferably 10 $mbar_{(abs.)}$, particularly preferably 50 $mbar_{(abs.)}$), and wherein at least two of the distillation columns are thermally coupled, in that heat from the condensation of the vapours from the distillation column with the higher head pressure is used directly or indirectly to heat the bottom stream from the distillation column with the lower head pressure. This allows for efficient separation of phenol and other potential high boiling secondary components.

BRIEF DESCRIPTION OF THE DRAWINGS

Various features and characteristics of the inventions described in this specification may be better understood by reference to the accompanying figures, in which.

DETAILED DESCRIPTION

Figure 1:
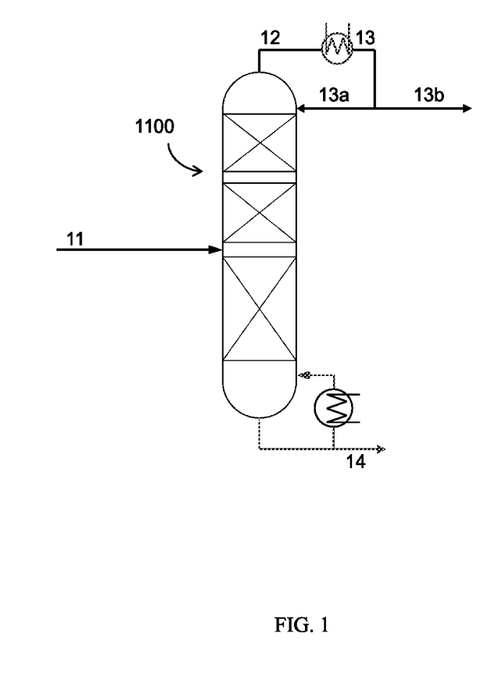
FIG. 1 shows a distillation scheme of the prior art for the purification of crude aniline.
Figure 2:
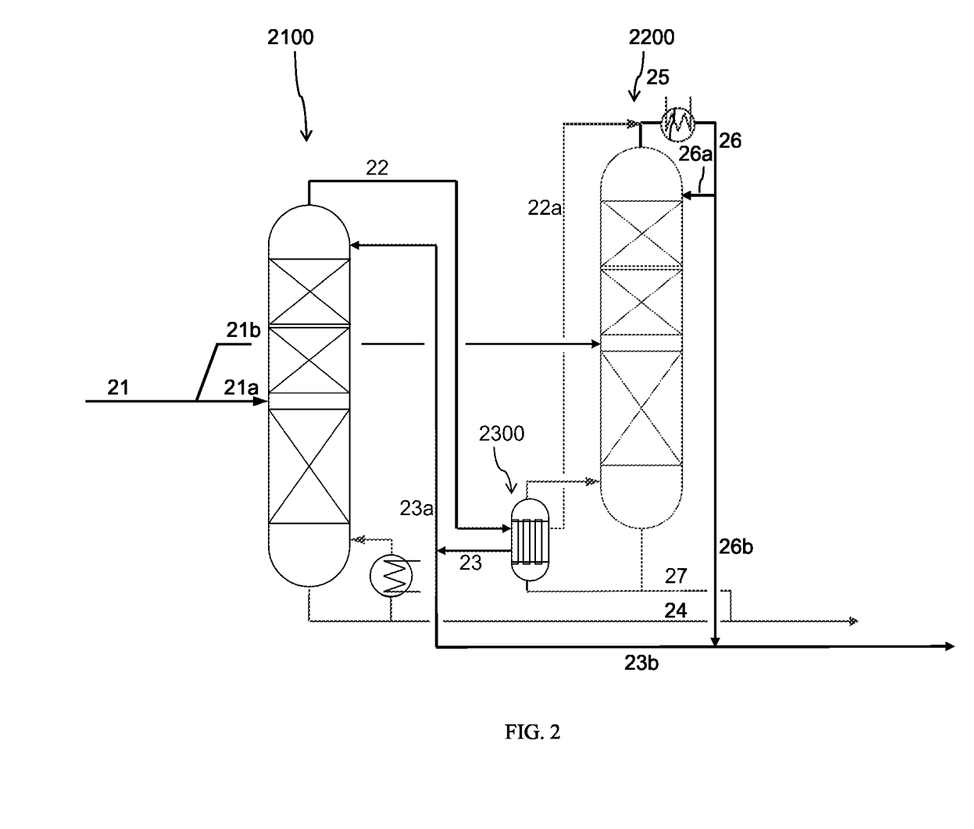
FIG. 2 shows a distillation scheme which is suitable for carrying out steps c) and d) of the process in accordance with the invention.

In the accompanying drawings:
FIG. 1 shows a distillation scheme of the prior art for the purification of crude aniline;
FIG. 2 shows a distillation scheme which is suitable for carrying out steps c) and d) of the process in accordance with the invention.

Firstly, a brief summary of the various possible embodiments will be given.

In a first embodiment of the invention, which may be combined with all of the other embodiments, the provision of the crude aniline fraction in step a) comprises distilling an aniline fraction which contains water and low boilers in addition to phenol, wherein the crude aniline fraction to be provided in step a) is obtained as a bottom product from this distillation and, with respect to its total weight, contains a maximum of 0.50% by weight of water, preferably a maximum of 0.20% by weight of water, particularly preferably a maximum of 0.10% by weight of water and more preferably 0.05% by weight of water. Preferably, with respect to its total weight, this crude aniline fraction contains a maximum of 0.100% by weight of benzene, particularly preferably a maximum of 0.010% by weight of benzene and more particularly preferably a maximum of 0.001% by weight of benzene.

In a second embodiment of the invention, which is a particular configuration of the first embodiment, the aniline fraction containing water and low boilers in addition to phenol is obtained as an organic phase by catalytic hydrogenation of nitrobenzene, followed by a phase separation into an organic and an aqueous phase, wherein in particular, the crude aniline fraction obtained as the bottom product from the distillation of this organic phase, with respect to its total weight, contains a maximum of 0.300% by weight of organic compounds which boil at lower temperatures than aniline (what are known as low boilers), preferably a maximum of 0.200% by weight of low boilers and particularly preferably a maximum of 0.100% by weight of low boilers.

In a third embodiment of the invention, which may be combined with all of the other embodiments, the crude aniline fraction in step b) is divided into exactly two partial streams, which are distilled in step c) in exactly two distillation columns.

In a fourth embodiment of the invention, which is a particular configuration of the third embodiment, the second distillation column is operated at a head pressure in the range from 50 $mbar_{(abs.)}$ to 300 $mbar_{(abs.)}$, preferably in the range from 80 $mbar_{(abs.)}$ to 200 $mbar_{(abs.)}$, particularly preferably in the range from 100 $mbar_{(abs.)}$ to 150 $mbar_{(abs.)}$.

In a fifth embodiment of the invention, which is a particular configuration of the third and fourth embodiments, the first distillation column is operated at a head pressure in the range from 250 $mbar_{(abs.)}$ to 500 $mbar_{(abs.)}$, preferably in the range from 270 $mbar_{(abs.)}$ to 400 $mbar_{(abs.)}$, particularly preferably in the range from 280 $mbar_{(abs.)}$ to 350 $mbar_{(abs.)}$.

In a sixth embodiment of the invention, which is a particular configuration of the third, fourth and fifth embodiments, the first distillation column is operated at a head pressure which is 80 $mbar_{(abs.)}$ to 300 $mbar_{(abs.)}$, preferably 100 $mbar_{(abs.)}$ to 200 $mbar_{(abs.)}$, particularly preferably 110 $mbar_{(abs.)}$ to 170 $mbar_{(abs.)}$ higher than the head pressure of the second distillation column.

In a seventh embodiment of the invention, which is a particular configuration of the third, fourth, fifth and sixth embodiments, at least part of the condensation of the aniline distillate from the first distillation column and the vaporisation of the first portion of the bottom stream from the first distillation column is carried out in one and the same heat exchanger.

In an eighth embodiment of the invention, which is a particular configuration of the third, fourth, fifth, sixth and seventh embodiments, the proportion of the crude aniline fraction provided in step a) which is distilled in the first distillation column is 5.00% to 49.00%, preferably 15.00% to 45.00%, particularly preferably 25.00% to 40.00% of the crude aniline fraction provided in step a), wherein the remaining proportion is distilled in the second distillation column.

In a ninth embodiment of the invention, which is a particular configuration of the third, fourth, fifth, sixth, seventh and eighth embodiments, the ratio of the recycle stream to the product stream in the second distillation column is lower than in the first distillation column.

In a tenth embodiment of the invention, which is a particular configuration of the third, fourth, fifth, sixth, seventh, eighth and ninth embodiments, a portion of the gaseous aniline distillate removed from the first distillation column is condensed in a condenser together with the gaseous aniline distillate removed from the second distillation column.

In an eleventh embodiment of the invention, which may be combined with all of the other embodiments, the process comprises the further step of:

e) using the heat generated during the condensation of the gaseous aniline distillate removed from the second distillation column for the production of steam and/or for heating a separation column in which an aniline-water azeotrope is removed from an aniline-containing effluent.

In a twelfth embodiment of the invention, which is a particular configuration of the eleventh embodiment, the separation column is operated at a head pressure in the range from 0.80 bar$_{(abs.)}$ 1.20 bar$_{(abs.)}$, preferably in the range from 1.00 bar$_{(abs.)}$ to 1.10 bar$_{(abs.)}$.

In a thirteenth embodiment of the invention, which may be combined with all of the other embodiments, the crude aniline fraction provided in step a), with respect to the total weight of aniline and phenol in the crude aniline fraction, contains 95.000% by weight to 99.995% by weight of aniline and 0.005% by weight to 5.000% by weight of phenol.

In a fourteenth embodiment of the invention, which may be combined with all of the other embodiments, for each distillation column, the first partial stream of the condensed aniline distillate is returned as a reflux stream to that distillation column from which the aniline distillate was removed (i.e. the reflux is returned to the original distillation column).

The embodiments briefly outlined above and further possible configurations of the invention will now be described in more detail below. In this regard, the embodiments may be combined with each other in any manner unless the context indicates otherwise.

The current customary industrial processes of the prior art for the production of aniline (in particular the hydrogenation of nitrobenzene, to a small extent the reduction of nitrobenzene with non-noble metals such as iron, as well as—nowadays of only small significance—the ammonolysis of phenol or chlorobenzene), despite their differences, all in the end deliver a phenol-containing crude aniline, so that the process in accordance with the invention may be usefully applied to all of these production processes, and thus the crude aniline to be provided in step a) may also originate from all of these processes.

Prior to drying which is regularly carried out in the prior art, in addition to phenol (and potentially other high boilers), it still generally contains at least low boilers and water. The term "low boilers" in the context of the present invention should be understood to mean those organic compounds (and potentially azeotropes) which have a lower boiling point than aniline under the pressure conditions selected for a distillation. In respect of the boiling behaviour, water is of course categorised as a low boiler; however, because this is not an organic impurity which is due to a secondary reaction, but is either a coupling product of aniline production (hydrogenation of nitrobenzene, ammonolysis of phenol), or is introduced with the reagents employed (reduction of nitrobenzene with non-noble metals such as iron in the presence of hydrochloric acid, ammonolysis with aqueous ammonia), then in general and also in the context of the present invention, it is listed separately. Typical low boilers are cyclohexylamine, cyclohexanone, cyclohexanol and benzene. Correspondingly, the term "high boilers" in the context of the present invention should be understood to mean those organic compounds (and possibly azeotropes) which have a higher boiling point than aniline under the conditions selected for a distillation. Under the conditions of the inventive distillation in accordance with step b) (head pressure a maximum of 500 mbar$_{(abs.)}$; excess of aniline), phenol is categorized as a high boiling azeotrope along with aniline. Other typical high boilers are aminophenols, toluidine, phenylenediamine, diphenylamine, N-cyclohexylaniline or even unreacted starting material from the production, for example nitrobenzene.

Because current aniline production processes initially provide a product which in general, in addition to phenol (and possibly other high boilers) still at least contains low boilers and water, preferably, step a) comprises a distillation in order to deplete the low boilers and water as far as possible. In this regard, the crude aniline fraction to be provided in step a) is obtained from this distillation as the bottom product. The distillation is operated in a manner such that water is separated as completely as possible, so that the crude aniline fraction which is generated as the bottom product, with respect to its total weight, contains water (determined by Karl Fischer titration) in the range from 0.00% by weight to 0.50% by weight, preferably 0.00% by weight to 0.20% by weight, particularly preferably 0.00% by weight to 0.10% by weight and more preferably 0.00% by weight to 0.05% by weight, especially 0.01% by weight to 0.05%.

In a preferred configuration of step a) of the process in accordance with the invention, this distillation is carried out in a rectification column which may preferably be operated at reduced pressure or at environmental pressure, particularly preferably at reduced pressure. The rectification column may be equipped with any devices known to the person skilled in the art for raising the separation efficiency (such as, in particular, fills, packing, trays and the like). The feed stream may be pre-heated; however this is not obligatory. Particularly preferably, a rectification column with a side stream is used, wherein the low boilers are distilled overhead. After condensation and phase separation, the aqueous phase is sent to the column as a recycle, so that finally, an aniline-water azeotrope is removed as a side stream. A dry aniline which is depleted in low boilers is obtained from the bottom of the rectification column.

The actual production of the aniline to be purified is preferably carried out by catalytic hydrogenation of nitrobenzene. In addition to aniline and secondary components, the crude process product obtained in this manner contains substantial proportions of water as the coupling product of the hydrogenation (reaction water), and therefore undergoes a phase separation. The aqueous phase obtained thereby contains the major portion of the reaction water (up to a residual quantity which cannot be separated by phase separation because of the slight solubility of water in aniline) and is separated. In addition to aniline, the remaining organic phase still contains low boilers and dissolved water. Typical low boilers are cyclohexylamine, cyclohexanone and benzene, wherein in general, the majority of the low boilers is made up of benzene. In general, the organic phase contained in the phase separation, with respect to its total weight, contains a maximum of 2.00% by weight of benzene (i.e. 0.00% by weight to 2.00% by weight, and similarly for the other values), preferably a maximum of 1.00% by weight of benzene, particularly preferably a maximum of 0.50% by weight of benzene. In principle, this organic phase may be used as the crude aniline fraction in step a). As already mentioned, however, it is preferable for this organic phase to undergo a distillation in order to deplete it in low boilers and water. The crude aniline fraction obtained as the bottom product from this distillation in particular contains, with respect to its total weight, a maximum of 0.300% by weight of organic compounds which boil at a lower temperature than aniline (what are known as low boilers), preferably a maximum of 0.200% by weight of low boilers and particularly preferably a maximum of 0.100% by weight of low boilers. In particular, the benzene content with respect to the total weight of the crude aniline fraction is preferably a maximum of 0.100% by weight, particularly preferably a maximum of 0.010% by weight and more particularly preferably a maximum of 0.001% by weight of benzene.

In step b), the crude aniline fraction provided in step a), in particular as the bottom product obtained from a distillation, is divided into two or more, preferably into two or three, particularly preferably into exactly two partial streams.

In step c), the partial streams of the crude aniline fraction obtained in step b) are distilled. The distillation of each partial stream is carried out continuously. The number of distillation columns corresponds to the number of partial streams. Thus, in step b), two or more, preferably two or three, particularly preferably exactly two distillation columns are used. Independently of the number of distillation columns, in accordance with the invention, none of the distillation columns employed in step e) is operated at a head pressure of more than 500 mbar$_{(abs.)}$, preferably more than 400 mbar$_{(abs.)}$, particularly preferably more than 350 mbar$_{(abs.)}$. This ensures that phenol is concentrated in the bottom stream from the distillation column as a high boiler and that purified aniline can be withdrawn overhead. The lower pressure limit is 1.0 mbar$_{(abs.)}$, preferably 10 mbar$_{(abs.)}$, particularly preferably 50 mbar$_{(abs.)}$. In this regard, this ensures that the diameter of the distillation columns employed does not have to be selected to be excessively large. Furthermore, by limiting the pressure at the lower end, the expenditure in the condensation of the initially gaseous distillate which is generated is kept within acceptable limits and avoiding too low a condensation temperature means that the heat that is released can be used efficiently.

In the following paragraphs, the invention will be explained with the aid of the most preferred embodiment with exactly two distillation columns. Starting from this representation, the person skilled in the art will find it easy to transpose the invention to configurations with more than two distillation columns. (The previously mentioned technical limiting conditions regarding the maximum head pressure for the columns are unchanged even for configurations with more than two columns, and in each case the condensation heat from the vapour stream from one column is used in order to heat the column with the next lower head pressure. In this manner, therefore, only the heat requirements for the first column are reflected in the energy balance for purification. In this regard, it should be noted that the pressure difference between the columns is selected so as to be large enough so that there is a sufficient temperature difference between the condensation temperature of the vapours from one column and the vaporisation temperature of the bottoms from the next column. Naturally, therefore, it is not possible to couple together any number of columns. On the one hand, the pressure range which is available is limited and on the other hand, the additional possible energy savings due to a further column also decreases with the number of columns).

In the discussion below relating to the embodiment with two distillation columns, the distillation column which is operated at a higher head pressure will be designated the "first distillation column", and the distillation column which is operated at a lower head pressure will be designated the "second distillation column".

Both in the first and also in the second distillation column, gaseous aniline is removed as the head product and subsequently condensed. A portion of the condensate obtained thereby is returned as a recycle stream to the starting distillation column and/or to the respective other distillation column, preferably to the starting distillation column; the proportion which is not recycled is the desired product from the corresponding distillation column, i.e. the product from the process in accordance with the invention. Similarly, both in the first and also in the second distillation column, a liquid bottom stream which is concentrated in phenol is obtained. A first portion of this bottom stream is respectively at least partially vaporised and at least a portion is returned to the respective distillation column, while a second portion of the bottom stream is discharged continuously or discontinuously (i.e. removed from the process). Preferably, that proportion of the first partial stream which is returned to the distillation column is present in the gaseous form (possibly except for small proportions of entrained droplets).

In order to carry out the process in accordance with the invention, advantageously, the second distillation column is operated at a head pressure in the range from 50 mbar$_{(abs.)}$ to 300 mbar$_{(abs.)}$, preferably in the range from 80 mbar$_{(abs.)}$ to 200 mbar$_{(abs.)}$, particularly preferably in the range from 100 mbar$_{(abs.)}$ to 150 mbar$_{(abs.)}$. This pressure range is selected in a manner such that on the one hand the vapours (i.e. here the gaseous purified aniline which is generated; this is the case for all distillation columns in step c)) have a condensation temperature which allows the heat released from condensation to be used efficiently. On the other hand, at a higher pressure, the separation efficiency of the distillation column with respect to the phenol/aniline mixture decreases, so that a higher recycle ratio and thus a higher input of energy is necessary in order to achieve the separation objectives.

The first distillation column is preferably operated at a head pressure in the range from 250 mbar$_{(abs.)}$ to 500 mbar$_{(abs.)}$, particularly preferably in the range from 270 mbar$_{(abs.)}$ to 400 mbar$_{(abs.)}$, more particularly preferably in the range from 280 mbar$_{(abs.)}$ to 350 mbar$_{(abs.)}$. In this regard, particularly advantageously, the head pressure of the first distillation column is 80 mbar$_{(abs.)}$ to 300 mbar$_{(abs.)}$, preferably 100 mbar$_{(abs.)}$ to 200 mbar$_{(abs.)}$, particularly preferably 110 mbar$_{(abs.)}$ 170 mbar$_{(abs.)}$ higher than the head pressure of the second distillation column. This ensures that the to condensation of the vapours takes place at a temperature level which is above the bottom temperature of the second distillation column, and therefore the released condensation heat can be used to heat the bottom of the second distillation column.

Advantageously, the proportion of the crude aniline fraction provided in step a) which is distilled in the first distillation column is 5.00% to 49.00%, preferably 15.00% to 45.00%, particularly preferably 25.00% to 40.00% of the crude aniline fraction provided in step a), and the remaining proportion is distilled in the second distillation column. Surprisingly, it has been shown that this distribution generally results in the best possible energy efficiency, which means that the condensation heat from the vapours from the first distillation column is just sufficient to provide the energy necessary for heating the bottom of the second distillation column. If a smaller proportion of the crude aniline fraction is supplied to the first distillation column, then in general, the second distillation column would require additional heating by different means, for example using steam from other processes. If a larger proportion of the crude aniline fraction is supplied to the first distillation column, then in general, more heat is available from the condensation of the vapour than is necessary for heating of the bottom of the second distillation column. Unless there are other possibilities for use, this superfluous heat then has to be released, for example as waste heat via an air cooler into the atmosphere.

In a further preferred embodiment of the process in accordance with the invention, the second distillation column is operated with a lower reflux ratio than that of the first distillation column, which means that the ratio of the reflux stream to the product stream in the second distillation column is smaller than in the first distillation column. This embodiment again results in the end in an operation which is optimized towards energy efficiency. In the pressure range which is relevant to the process, the difference between the boiling temperatures of phenol and aniline increases with decreasing pressure, so that the separation efficiency of the distillation columns also improves at lower pressure and, therefore, a smaller reflux ratio is sufficient to comply with the target phenol specification in the pure aniline. For each of the distillation columns, any condensed aniline distillate from one of the distillation columns or any mixture of the condensed distillates may be used as the reflux medium, as long as it complies with the phenol specification for the purified aniline.

In a preferred embodiment, the first distillation column is a packed column with a rectifying section and a stripping section, wherein the rectifying section preferably has 5 to 30, particularly preferably 10 to 25 and more particularly preferably 15 to 20 theoretical separation stages. The stripping section preferably has 20 to 60, particularly preferably 25 to 40 and more particularly preferably 28 to 37 theoretical separation stages. In a preferred embodiment of the invention, a partial stream of the vapours from the first distillation column can be supplied to the condenser for the vapours from the second distillation column via a pipeline, which preferably contains a control valve, i.e. a portion of the purified gaseous aniline removed from the first distillation column is condensed in a condenser together with the purified gaseous aniline removed from the second distillation column. In this manner, on the one hand, the head pressure in the first distillation column can be regulated and on the other hand, under the prevailing pressure and temperature conditions, non-condensable proportions of gas (for example ammonia) are prevented from becoming accumulated in the system.

In an equally preferred embodiment, the second distillation column is a packed column with a rectifying section and a stripping section, wherein the rectifying section preferably has 5 to 30, preferably 10 to 25 and more particularly preferably 15 to 20 theoretical separation stages. The stripping section preferably has 20 to 60, particularly preferably 25 to 40 and 28 to 37 theoretical separation stages. The aniline vapours are removed from the head of the column in the gaseous form and condensed in at least one condenser (which may be configured as a cascade of several condensers). Under the prevailing pressure and temperature conditions, uncondensed fractions are removed from the system as effluent gas and, for example, treated in a thermal exhaust air purification plant.

In step d) of the process in accordance with the invention, the heat released during condensation of the aniline distillate from the first distillation column is used to provide the heat required for vaporisation of the first portion of the bottom stream from the second distillation column (heat integration). In this regard, it is not absolutely necessary to use the entirety of the gaseous overhead product from the first distillation column for this heat integration. In the case in which not all of the gaseous overhead product is required to carry out the heat integration, a portion thereof may simply be condensed, in fact preferably by feeding it to the condensation of the gaseous overhead product from the second distillation column, thereby becoming a material component thereof.

It is possible to carry out the exchange of heat from the vapours from the first distillation column in order to heat the second distillation column indirectly (i.e. by means of an additional heat carrier medium), by initially using the condensation heat to produce steam and then in turn to use it to heat the second distillation column. Preferably, however, the exchange of heat is direct (i.e. without an additional heat carrier medium). In accordance with the invention, this is carried out by means of one or more external evaporators such as, for example, circulating evaporators.

In a preferred embodiment of the invention, the heat integration of step d) is accordingly carried out by using a heat exchanger in which the gaseous aniline distillate removed from the first distillation column is condensed and also the first portion of the bottom stream from the second distillation column is vaporised, which means that condensation and vaporisation are carried out in one and the same heat exchanger. Thus, the heat exchanger carries out the function of an evaporator-condenser. Because of the small differences in temperature, particularly preferably, the bottom product to be vaporised is conveyed through the heat exchanger by means of a pump as a forced circulation. Particularly preferably, tubular heat exchangers are used, wherein the condensation expediently occurs on the shell side and the vaporisation occurs on the tube side of the heat exchanger.

In this manner, the heat exchanger used as the evaporator-condenser heats the second distillation column by transferring the condensation heat from the vapours out of the first distillation column onto the bottoms from the second distillation column with partial vaporisation thereof.

In a further embodiment of the invention, the vapours from the second distillation column may be used at least in part in a step e) in order to produce (in particular low pressure) steam during their condensation, utilising the condensation heat being released. These vapours may also be utilised in order to heat a separation column in which an aniline-water azeotrope is removed from an aniline-containing effluent in a thermal separation procedure (separation column). This may occur either by direct heat transfer or by means of indirect heat transfer via previously generated steam. Preferably, the heat is transferred directly.

The aniline-containing effluent is preferably what is known as process water, which is generated during the hydrogenation of nitrobenzene as a further product in addition to aniline and preferably is separated from the major portion of the organic crude product by a phase separation at a temperature in the range from 20° C. to 45° C. The aniline-water azeotrope from the effluent separation column (the aniline content of which is significantly higher compared with that of the starting effluent) is condensed and then preferably undergoes a phase separation. Particularly preferably, this phase separation occurs together with the crude product of water and aniline generated in a hydrogenation of nitrobenzene to aniline. Any ammonia which might be present can be supplied to an exhaust air purification plant in the gaseous form together with other inert gases by appropriate selection of the condensation conditions.

If the condensation heat from the vapours from the second distillation column is used to heat an effluent separation column, then this may be carried out indirectly by firstly producing steam and then using this for heating. Steam produced in this manner can clearly also be used to heat any other equipment or can be used for steam stripping.

Preferably, however, the vapours from the second distillation column are used directly in order to heat an effluent separation column of this type. In this regard, a heat exchanger functioning as an evaporator-condenser like in the preferred embodiment of step d) is used which transfers the condensation heat to the bottoms from the effluent separation column. Preferably, the evaporator-condenser is configured as a tubular heat exchanger and the condensation of the vapours is preferably carried out on the shell side of the apparatus, while the water from the bottom of the effluent separation column is conveyed by means of a pump to a distributor which distributes it onto the inside of the tubes. Potentially, if more heat is available from the vapours from the second distillation column than is required to heat the effluent separation column, a partial stream of the vapours from the second distillation column is condensed in an air cooler. If the vapours from the second distillation column are not sufficient to provide the heat required to heat the effluent separation column, then this can be balanced by additional steam heating. The steam may either be guided directly into the bottom of the effluent separation column or be used to heat a second circulation evaporator at the bottom of the effluent separation column. In this manner, even transient conditions such as, for example, during start-up of the distillation system are feasible, without running the risk of producing effluent loaded with aniline.

As an example, a packed column may be used as the effluent separation column which preferably has 10 to 50 theoretical separation stages and particularly preferably 20 to 30 theoretical separation stages. Because of the lower boiling point of the aniline-water azeotrope compared with water, the purified water appears at the bottom of the packed column. The head pressure of the effluent separation column is preferably in the range from 0.80 $bar_{(abs.)}$ to 1.20 $bar_{(abs.)}$, particularly preferably in the range from 1.00 $bar_{(abs.)}$ to 1.10 $bar_{(abs.)}$.

EXAMPLES

The purification of the crude aniline fraction provided is described in the following examples. They were model computations determined using Aspen Plus® V7.3. For the crude aniline fraction which was provided, the composition given below was assumed in each case (the content data is given as the proportion by weight with respect to the total weight). The comparative examples which were modelled were distillations, in each case as a simple vacuum distillation at a head pressure of 120 $mbar_{(abs.)}$ or 300 $mbar_{(abs.)}$. The example in accordance with the invention which was modelled was the distillation with exactly two columns. In all cases, the reflux ratios were adjusted so that the distillate from each column had a phenol content of 50 ppm.

aniline: 99.76%
water: 100 ppm
other low boilers: 220 ppm
phenol: 700 ppm
high boilers: 1350 ppm Example 1 (Comparative Example)

A scheme in accordance with FIG. 1 was modelled. A rectifying section with 18 theoretical stages and a stripping section with 12 theoretical stages were considered for the column. The head pressure of the column (1100) was fixed at 120 $mbar_{(abs.)}$; the pressure drop over the column was 45 mbar. A crude aniline fraction (11) with the composition given above was supplied to it at a temperature of 125° C. between the stripping section and the rectifying section of the column. The vapour stream (12) leaving the head of the column was at a temperature of 117° C. and was condensed in its entirety by cooling to 110° C. (13). A portion of this condensed stream (13) was supplied to the head of the column as the reflux (13a) and a further portion was taken off as the product (13b). The ratio of the reflux stream and product stream (R/E ratio; 13a/13b) was adjusted in a manner such that the phenol content in the product stream (13b) was 50 ppm with respect to the stream as a whole. This content could be obtained with a R/E ratio of 1.175. At the bottom of the column, a stream (14) containing 94% aniline, 4% high boilers and 2% phenol, respectively with respect to the stream as a whole, was discharged and a temperature of 126° C. was established. In order to heat the column bottom, a required specific heat output of 311 $KW/t_{crude\ aniline}$ was determined; the condensation of the vapours required a specific cooling capacity of 320 $kW/t_{crude\ aniline}$.

Example 2 (Comparative Example)

The simulation was carried out in a manner analogous to Example 1, with the difference being that the head pressure of the column (1100) was set at 300 $mbar_{(abs.)}$ (head temperature 143° C.). The bottom temperature was set at 148° C. The required R/E ratio for obtaining a phenol content of 50 ppm in the product stream (13b) was now 2.48. The required specific heat output for the distillation was 544 $KW/t_{crude\ aniline}$ and in order to condense the vapours (12), 552 $KW/t_{crude\ aniline}$ was required. The product composition which was determined corresponded exactly to that from Example 1.

Example 3 (in Accordance with the Invention)

A scheme in accordance with FIG. 2 was modelled. For both columns (2100, 2200) a respective rectifying section with 18 theoretical stages and a stripping section with 12 theoretical stages were considered. The head pressure for the first column (2100) was established at 300 $mbar_{(abs.)}$, the pressure drop over the column was established at 45 mbar. The head pressure for the second column (2200) was set at 120 $mbar_{(abs.)}$ and the pressure drop over the column was set at 45 mbar. A crude aniline fraction (21) with the composition given above was divided into two partial streams in a ratio of 64:36, wherein the smaller stream (21a) was supplied between the stripping section and the rectifying section of the first column (2100) and the larger stream (21b) was supplied between the stripping section and the rectifying section of the second column (2200). At the bottom of the column, a respective stream (24, 27) containing 94% aniline, 4% high boilers and 2% phenol, respectively with respect to the whole stream, was discharged and in the first column (2100) a bottom temperature of 148° C. was established while in the second column (2200) a bottom temperature of 126° C. was established. For each of the columns (2100, 2200), the R/E ratio was adjusted so that in each case a product stream (23b, 26b) with a phenol content of 50 ppm with respect to the whole product stream was produced. The composition of the product stream was again the same as in Examples 1 and 2. In this regard, a R/E ratio of 2.94 was necessary in the first column, while in the second column, a R/E ratio of 1.24 was necessary. The head temperatures in the two columns were 143° C. for the first column and 117° C. for the second column, respectively.

The vapours (22) for the first column (2100) could be 99.85% condensed at a condensation temperature of 141° C. In this regard, almost the entire condensation heat accrued at a temperature level which enabled the heat to be used to heat the second column (2200), which had a bottom temperature of 126° C., 15K below the condensation temperature of the first column. The fractions remaining in the gas phase were additionally fed into the condensation apparatus of the second column and condensed therein.

For the condensation of the vapours (25) from the second column (2200) in addition to the uncondensed portion (22a) from the first column (2100) leaving the heat exchanger (2300), which served to heat the bottom of the second column (2200), a specific cooling capacity of 201 KW/$t_{crude\ aniline}$ was necessary. In the model, the vapours could be completely condensed at a temperature of just 114° C. Thus, this condensation temperature was 14K above the boiling point of water at atmospheric pressure, so that the energy could be used to vaporise water, for example, at atmospheric pressure, which also enables further energy integration.

For the purposes of energy balance, it can be seen that in order to heat the first column (2100), a specific heat output of 201 KW/$t_{crude\ aniline}$ was required. The specific heat output for the second column (2200) was 196 KW/$t_{crude\ aniline}$. This was available in its entirety from the condensation of the vapours from the first column, requiring a specific cooling capacity of identical value. In total, therefore, the required specific heat output could be reduced by approximately one third by means of the process in accordance with the invention.

The invention claimed is:

1. A process for preparing pure aniline, comprising:
 a) providing a crude aniline fraction containing 80.000% by weight to 99.999% by weight of aniline and 0.001% by weight to 20.000% by weight of phenol, based on the total weight of aniline and phenol in the crude aniline fraction;
 b) dividing the crude aniline fraction into a first partial stream and a second partial stream;
 c) distilling the first partial stream in a first distillation column and distilling the second partial stream in a second distillation column, wherein the first distillation column is operated at a higher head pressure than the second distillation column, with the proviso that each of the first distillation column and the second distillation column is operated at a head pressure in the range from 1.0 $mbar_{(abs.)}$ to 500 $mbar_{(abs.)}$, and wherein from each of the first and the second distillation column,
   a gaseous aniline distillate is removed as the overhead product and subsequently condensed, wherein a first partial stream of the condensed aniline distillate is returned to the first and/or the second distillation column as a reflux stream and a second partial stream of the condensed aniline distillate is removed as the product stream, and
   a liquid bottom stream which is concentrated in phenol is removed, from which a first portion is partially or completely vaporised and is returned to the distillation column it originated from, and from which a second portion is discharged; and
 d) using the heat released during the condensation of the aniline distillate from the first distillation column to provide the heat necessary for vaporising the first portion of the bottom stream from the second distillation column.

2. The process of claim 1, in which the provision of the crude aniline fraction comprises distilling an aniline fraction which contains water and low boilers, and to phenol, wherein the crude aniline fraction is obtained as a bottom product from such distillation and contains a maximum of 0.50% by weight of water, based on the total weight of the crude aniline fraction.

3. The process of claim 2, in which the aniline fraction containing water, low boilers, and to phenol is obtained as an organic phase by the catalytic hydrogenation of nitrobenzene, followed by a phase separation into the organic phase and an aqueous phase.

4. The process of claim 1, in which the crude aniline fraction is divided into exactly two partial streams which are distilled in in exactly two distillation columns.

5. The process of claim 4, in which the second distillation column is operated at a head pressure in the range from 50 $mbar_{(abs.)}$ to 300 $mbar_{(abs.)}$.

6. The process of claim 4, in which the first distillation column is operated at a head pressure in the range from 250 $mbar_{(abs.)}$ to 500 $mbar_{(abs.)}$.

7. The process of claim 4, in which the first distillation column is operated at a head pressure which is 80 $mbar_{(abs.)}$ to 300 $mbar_{(abs.)}$ higher than the head pressure of the second distillation column.

8. The process of claim 4, in which at least part of the condensation of the aniline distillate from the first distillation column and the vaporisation of the first portion of the bottom stream from the first distillation column is carried out in the same heat exchanger.

9. The process of claim 4, in which the proportion of the crude aniline fraction which is distilled in the first distillation column is 5.00% to 49.00% of the crude aniline fraction and the remaining proportion is distilled in the second distillation column.

10. The process of claim 4, in which the ratio of the reflux stream to the product stream in the second distillation column is lower than in the first distillation column.

11. The process of claim 4, in which a portion of the gaseous aniline distillate removed from the first distillation column is condensed in a condenser together with the gaseous aniline distillate removed from the second distillation column.

12. The process of claim 1, further comprising:
 e) using the heat released during the condensation of the gaseous aniline distillate removed from the second distillation column for the production of steam and/or for heating a separation column in which an aniline-water azeotrope is removed from an aniline-containing effluent.

13. The process of claim 12, in which the separation column is operated at a head pressure in the range from 0.80 $bar_{(abs.)}$ to 1.20 $bar_{(abs.)}$.

14. The process of claim 1, in which the crude aniline fraction contains 95.000% by weight to 99.995% by weight of aniline and 0.005% by weight to 5.000% by weight of phenol, based on the total weight of the aniline and phenol in the crude aniline fraction.

15. The process of claim 1, in which the first partial stream of the condensed aniline distillate of each distillation column is returned as a reflux stream to the distillation column from which the aniline distillate was removed.

* * * * *